United States Patent [19]

Frásch et al.

[11] Patent Number: 5,578,449

[45] Date of Patent: Nov. 26, 1996

[54] PROCEDURE FOR THE SEX DETERMINATION OF EMBRYOS IN MAMMALS ESPECIALLY APPLIED TO BOVINE EMBRYOS

[75] Inventors: Alberto C. Frásch; Rodolfo A. Ugalde, both of Buenos Aires, Argentina

[73] Assignee: Hilding Ohlsson, S.A., Buenos Aires, Argentina

[21] Appl. No.: 425,711

[22] Filed: Apr. 20, 1995

Related U.S. Application Data

[63] Continuation of Ser. No. 868,995, Apr. 15, 1992.

[30] Foreign Application Priority Data

Oct. 3, 1991 [AR] Argentina ................................. 320.843

[51] Int. Cl.$^6$ .............................. C12Q 1/68; C12P 19/34; C07H 21/04
[52] U.S. Cl. ........................... 435/6; 435/91.2; 536/24.3; 536/24.33
[58] Field of Search ................................ 436/6; 435/91.2, 435/78

[56] References Cited

U.S. PATENT DOCUMENTS 5,055,393 10/1991 Kwoh et al. ................................. 435/6
5,461,145 10/1995 Kudo et al. .......................... 536/24.31

OTHER PUBLICATIONS

A. H. Handyside et al *Nature* vol 344, 768 (1990) "Pregnancies from biopsied human preimplantation embryos by specific DNA amplification".

M. W. Bradbury et al, *Proc Natl Acad. Sci.* 87, 4053 (1990) "Enzymatic amplification of a Y chromosome repeat in a single blastomere allows identification of the sex of preimplantation mouse embryos".

H. A. Ehrich et al., *Science* 252, 1643 (1991) "Recent Advances in the Polymerase Chain Reaction".

J. D. Watson et al. *Recombinant DNA* Second Edition, Chapter 6 "The Polymerase Chain Reaction" Scientific American Books, W. H. Freeman & Co. (1992).

Palmer et al. Comparison Of Human ZFY And ZFX Transcripts, PNAS 87:1681–1685.

Pollevick et al. Sex Determination Of Bovine Embryos By Reastriction Fragment Polymorphisms Of PCR Amplified ZFX/ZFY Loci, Biotechnology 10: 805–807.

Peura et al. Theriogenology 35: 547–555.

Albeut et al., J. Clin. Microbiol 28: 1560–1564.

Aurelius et al, The Lancet, 337(8735), Jan. 26, 1991, pp. 189–192.

*Primary Examiner*—Stephanie W. Zitomer
*Assistant Examiner*—Dianne Rees
*Attorney, Agent, or Firm*—Alfred M. Walker

[57] ABSTRACT

A procedure is provided for the sex determination of embryos in mammals, that is particularly exemplified on bovines. The procedure overcomes the limitations given in former techniques. It includes a new stage of polymerase chain reaction PCR method, using specific oligonucleotides in order to amplify fragments corresponding to the sampled cells and not from false ones, spuriously produced. In this way, the necessary sensitivity is obtained. The oligonucleotides sequences are particularly selected for the procedure. The procedure is used for the sex determination of embryos in mammals, and the procedure is sensitive enough to be carried out a sample containing few cells, is highly secure, and which give positive results for both female and male sex; specially applied to bovine embryos.

2 Claims, 1 Drawing Sheet

```
5' ATAATCACATGGAGAGCCACAAGCTTACCAGCAAGTCAGAGAAGGCCATCG
   ATAATCACATGGAGAGCCACAAGCTTACCAGCAAG?GXGAGAAGXCCATTG
   |_____|                    |__|
             XY/1

AATGTGATGACTGTGGGAAGCATTTCTCCCATGCTGGGGCTTTGTTCACTC
   AATXCGATGAGTGCGGAAAGCATTTCTCTCATGCTGGGGCTTTGTTTACTC
   |_____|
         N/XY1

ACAAAATGGTGCATAAGCAAAAACCACCCAGCAAAATGCATAAATGTAAAT
   ATAAAATGGTGCATAAGGAAAAAGGAGCTAACAAAATGCACAAATGTAAAT

TCTGTGAGTATGAGACAGCTGAACAAGGGTTATTAAATCGCCACCTTTTGG
   TCTGTGAATACGAGACAGCTGAACAAGGGTTACTGAATCGCCACCTTTTGG

CAGTCCACAGCAAGAACTTTCCCCATATATGTGTAGAGTGTGGTAAAGGTT
   CGGTCCATAGCAAGAACTTTCCTCATATATGCGTGGAGTGTGGTAAAGGTT

TTCGTCACCCATCAGAGCTCAAAAAGCACATGCGAATCCATACTGGAGAGA
   TTCGTCATCCATCAGAGCTCAAAAAGCACATGCGAATCCATACTGGCGAGA
                                       ↓∝
                                       |____|
   AACCGTACCAATGCCAGTACTGCGAATATAGGTCTGCAGACTCTTCTAATT
   AGCCGTACCAGTGCCAGTACTGCGAATATAGGTCCGCAGACTCTTCTAACT

TGAAGACGCATGTGAAAACTAAGCATAGTAAAGAAATGTCTTTCAAGTGTG
   TGAAAACGCATGTAAAAACTAAGCATAGTAAAGAGATGCCATTCAAGTGTG
                                                  |__|

ACATTTGTCTTCTGACTTTCTCAGATACCAAAGAAGTGC
   ACATTTGTCTTCTGACTTTCTCAGATACCAAAGAAGTGC  3'
   |_____|    |_____|
      N/XY-2              XY/2
```

FIG. 1

PROCEDURE FOR THE SEX DETERMINATION OF EMBRYOS IN MAMMALS ESPECIALLY APPLIED TO BOVINE EMBRYOS

This application is a continuation of application Ser. No. 07/868,995, filed Apr. 15, 1992.

INTRODUCTION

1. Field of Application

The present invention refers to a novel procedure for the sex determination of embryos in mammals, especially as applied to bovine embryos.

The improvement of cattle quality through crossbreeding of individuals with selected hereditary characteristics is a technique that has been used for quite a long time.

Artificial insemination techniques have lowered the costs involved since from a sole selected male a great number of offspring can be obtained.

However, these techniques are being supplanted quickly by embryo implantation in females, in which females are previously prepared for the implantation of an embryo. Implantation of frozen embryos has many advantages such as, for example, a greater breeder's performance, especially with females, changing the pregnancy periods according to the climatic seasons and according to commercial circumstances, as well as to providing greater facility in national and international home trade.

Nevertheless, these techniques run into a limitation in that the embryo's sex is not known even though it is determined at the moment of fertilization, so the embryos must be implanted, obtaining in this way an unpredictable result.

In the case of animals like bovines, determinating the embryo's sex will allow one to obtain advantages in cattle commercialization and exploitation.

2. Discussion of the Prior Art

The development of procedures to determine an embryo's sex have already been tried, but only poor and limited results have been obtained.

Some of these procedures are based on antigen-antibody reactions. Antibodies obtained against specific proteins which are only produced by embryos of one sex, and not of the other sex, are allowed to react with whole embryos and their reactivity is detected by a second antibody.

In such procedures, beside the sensitivity problems, there are uncertainties when the result is negative. This means that, when the result is positive, the antigen-antibody reaction guarantees that the cells of the sample belong to a determinated sex. But when the result is negative, it could be due to cells belonging to an embryo of the opposite sex, or caused by mistakes or imperfections while applying the technique. It is also possible to obtain a negative result if one of the reactants utilized is spoiled or destroyed, because of an excess in the temperature of the protein, an insufficient sample, etc.

The procedure of the present invention overcomes such obstacles as it gives a definitive result for each sex, and a different result when a mistake occurs during the application of the technique.

The rest of the experimental procedures are based, as in the present invention, on the analysis of the DNA of cells that have been sampled. The limitation, in the typical prior art DNA analysis procedures, comes from the fact that the sensitivity of the prior art method isn't enough, and the results are affected by the "noise" of molecules produced in secondary reactions.

For a better consideration of the problem, it is enough to say that the cells sampled never exceed 20, being normally 8 to 12 cells. A greater number of cells removed as samples would damage the embryo from which the cells are obtained.

Any cell of a higher mammal has about 2 pg ($2 \times 10^{-12}$ g) of DNA. The DNA could have about $2-3 \times 10^9$ base pairs. But a gene (for example, such as a sex determination gene) could have around 1000 pairs of bases, which means that it is necessary to analyze the millionth part of the DNA per cell.

Supposing 10 cells are sampled, the amount to be analyzed is of:

$$2\ pg \times 10 \times 10^{-6} = 20 \times 10{-18}\ g\ \text{of DNA}$$

In a human and a mouse it is possible to use the repetitive specific nucleotides sequences of Y chromosome, which here indicates that it is a male embryo ([1]A. H. Handyside et al., *Nature* 344, 768, 1990, and [2]M. W. Bradbury et al., *Proc. Natl. Acad. Sci.* 87, 4053, 1990), but these methods have the same uncertainty as regards to the one method indicated for antigen-antibody methods already mentioned.

Actually, the most promising procedures are based on the application of the Polymerase Chain Reaction (PCR) technique on the DNA of the sampled cells, since it was established that, in a homologous genome region of the X and Y chromosomes, there are differences in their sequence, making it possible to identify the embryo's sex ([2]). This technique, a DNA chain extension with Polymerase ([3]) H. A. Erlich et al., *Science* 252, 1643, 1991), consists of consecutive steps of amplification of a DNA fragment, in this particular case, a fragment located in the sex chromosome X/Y. For this, specific oligonucleotide primers are required. These techniques, described in detail farther on, have a limitation. Although the number of DNA fragments that will be finally detected, are doubled in each step, there comes a moment in which, for different reasons, a number of fragments, not related to the target fragment, is produced at the same time, and the unrelated fragments start to mask the desired result the present invention is looking for, i.e., such as by noise. In the case where the number of amplification steps is increased, the background would be greater.

Taking into account the limitation stated above, such procedures are not sensitive enough to determine the embryo's sex.

The present invention proposes a technique that overcomes the aforementioned limitations, as it adds a second step of PCR amplification with other oligonucleotide primers, allowing a subsequent amplification of the material already amplified in the first step. In this way, the necessary sensitivity is attained.

BRIEF DESCRIPTION OF THE PREFERRED EMBODIMENT

The present invention suggests a procedure with the following stages:

a) obtaining a mammal's embryo in its blastula stage of development, cutting, by means of microsurgery, the pellucidae area and extracting a sample containing from 8 to 19 cells, preferably from 8 to 12 cells;

b) separating by dissection the cells from the traces of the embryo's pellucidae membrane;

c) isolating and denaturing the DNA of the cells, inserting said cells in a tube with water, heating to 95° C., chilling immediately in ice and centrifuging to recover the condensed liquid, aqueous DNA solution;

d) submitting such aqueous DNA solution to a first round of the polymerase chain reaction (PCR) technique with a first pair of oligonucleotides able to act as "primers" to amplify a first fragment of DNA belonging to the sex chromosome in the presence of a polymerase as a specific enzyme and nucleotides, until a first amplified DNA solution is obtained;

e) submitting an aliquot of the first amplified DNA solution to a second round of PCR with a second pair of oligonucleotides able to act as "primers" to amplify a second fragment, internal to the first fragment amplified in the previous stage, until a second amplified DNA solution is obtained;

f) adding to the second amplified DNA solution a restriction enzyme, able to cut the amplified second fragment of the sexual chromosome DNA when it is a Y chromosome, and unable to cut it when it is an X chromosome;

g) fractionating according to size by means of electrophoresis in an agarose gel, staining with ethidium bromide and visualizing with UV (ultraviolet) light;

h) comparing with a standard molecular weight marker;

i) determining the embryo's sex according to the presence of only one band, with the same number of base pairs as the the second fragment of the sex chromosome DNA (female sex), or three bands, the first with the same number of base pairs as the second fragment of the sex chromosome DNA, the second and the third bands corresponding, each one, to a number of base pairs, which, added up, will give the same number of base pairs as the second fragment of the sex chromosome DNA (male sex);

The aforementioned first pair of oligonucleotide primers in stage d), second pair of oligonucleotide primers in stage e) and the restriction enzyme in stage f) are chosen beforehand in the following way:

I) determining the DNA sequence of the first fragment corresponding to the sex X and Y chromosome in stage d), and selecting the second DNA fragment, internal to the first fragment (without sharing any of the termini of the first fragment);

II) choosing a restriction enzyme able to cut the Y chromosome DNA second fragment and not cut the X chromosome DNA second fragment, according to the base sequence determined in step I);

III) choosing a first sequence of about 20 to 30 bases starting from the extreme 5' end of the first fragment, and a second sequence of about 20 to 30 bases starting from the extreme 3' end of the first fragment, the aforementioned first sequence and the complement of the aforementioned second sequence conforming to the sequence of bases of the first pair of oligonucleotide primers, according to the base sequence determined in step I);

IV) choosing a third sequence of about 20 to 30 bases starting from the extreme 5' end of the second fragment, and a fourth sequence of about 20 to 30 bases starting from the extreme 3' end of the second fragment, the third sequence and the complement of the mentioned fourth sequence conforming to the sequence of bases of the second pair of oligonucleotide primers, according to the base sequence determined in step I);

V) synthesizing in a "gene assembler" device, the aforementioned first and second pairs of oligonucleotide primers.

According to what has been described, referred to as prior art, the innovation brought to the present invention comprises mostly in the inclusion of stage e), that is, the additional round of PCR with specific oligonucleotide primers to amplify gene fragments corresponding to the original cells, that is, the fragments that were obtained in amplifying stage d).

The way in which the sequences of oligonucleotides are chosen is also a novelty.

Nevertheless, there are new details in other stages of the procedure that, related to bovines, were developed and optimized.

In one example, this exposition allows for the establishment of the basis for the development of techniques for use with the embryos of other mammals.

OBJECTS OF THE PRESENT INVENTION

It is, therefore, an object of the present invention, to provide a procedure to determine a mammalian embryo's sex which procedure is sensitive enough to carry out with a sample of a few cells.

Another object of the present invention is to provide a procedure to determine, in a highly reliable way, the sex of mammalian embryos, giving positive results for both female and male offspring, and not a confusing negative result, due to imperfections in its application.

And, finally, another object is to provide a procedure for the sex determination of embryos in mammals, especially applicable to bovine embryos.

BACKGROUND OF THE PRESENT INVENTION

Given that it is necessary to amplify a DNA fragment of the sex chromosome, to obtain enough sensitivity in order to determine the embryo's sex from a few sampled cells, it is necessary to discuss the molecular mechanisms of DNA amplification.

Any simple DNA chain has two terminals (or extremes), one of them with phosphate in carbon 5' of the deoxyribose molecule (extreme 5'), the other with hydroxyl in position 3' of the sugar (extreme 3'). At the same time, the complementary chain has the same kind of extremes in opposing positions, that is, the extreme 3' of a chain has the other 5' in front of it. For this reason, it is considered that the two complementary chains of a DNA molecule have opposite polarities and are antiparallel.

It is known that the replication of a DNA chain is produced by the combination of a nucleotide-5'-triphosphate with the extreme 3' of the chain. Therefore, this extreme 3' is the growing point of the DNA, and synthesis proceds in opposite directions in both complementary chains.

A template chain is simply a DNA chain. However, the template chain doesn't provide any extreme 3' able to promote the beginning of the growth of the new chain that is going to be synthesized. For this reason, the synthesis of a new DNA molecule is only possible in the presence of a nucleic acid fragment that can provide the extreme 3'. The name given to this nucleic acid fragment is "primer."

The DNA synthesis mechanisms discussed above require the action of a series of enzymes that catalyze the reaction. The existence of polymerases has been proven among the enzymes that have been identified.

The application to lab techniques of what has been discussed was perfected in the so-called PCR (Polymerase Chain Reaction) [3]. In each step of this technique, the number of chains obtained in the former step, is doubled, so this number has a geometric growth.

However, the application of this technique has one limitation derived from the synthesis, of spurious DNA fragments from the primers themselves which don't correspond to the template that one wants to copy. This can be attributed to contamination, as well as by other causes. But the correct copies of the template, as well as the false ones, have in their terminals the sequences of the primers themselves, which create complementary sequences that, in the next step, will be amplified. Therefore, in the following steps the target chains that are under consideration, as well as the false ones, amplify, and there comes a point where it is impossible to improve the sensitivity.

In the present invention's procedure, the polymerase chain reaction PCR technique is improved as follows.

After the first round of the polymerase chain reaction PCR technique on a DNA fragment, there comes a point in which it is impossible to improve the sensitivity of the technique. Experimentally, it was found that approximately 45 cycles is the upper limit of amplification.

To improve the relation between the number of similar chains of the original target and the number of false chains, it is necessary to distinguish the first ones, as the second ones won't necessarily be homogeneous. According to the present invention it is possible to do it looking for a smaller DNA fragment, whose sequence is a subsequece of the original sequence. For that purpose, other DNA chains, whose sequences correspond to sequences of the chains under consideration, are used as new primers. In this way, the polymerase chain reaction PCR technique is applied again, with its geometric growth, but only on the DNA amplified fragments that correspond to the original template.

DETAILED DESCRIPTION OF THE DRAWING

FIG. 1 shows the sequence (SEQ. ID. NO: 1 and 2) corresponding to a fragment of sex chromosomes experimentally obtained, superimposed by indications illustrating the choice of primers for the procedures of the present invention.

DETAILED DESCRIPTION

A typical example started with the use of bovine embryos in the blastula stage; and a sample of cells was obtained by microsurgery. The remaining pellucidae zone is put aside by dissection, as this area doesn't correspond to the embryo.

The sampled cells of the embryo were introduced in a tube with 30 μl of water and the sampled cells were denatured by heating them at 95° C., cooling immediately with ice and centrifuging to recover the condensed liquid.

To the aqueous DNA solution obtained in this way PCR was applied, but in two rounds with different oligonucleotide primer sequences.

To get to this point in the procedure, it was necessary to choose the sequence and synthesize the oligonucleotide primers, and for that reason the following steps were taken, in relation with FIG. 1.

In FIG. 1, shows the sequence of bases corresponding to a fragment of bovine chromosome, from the homologous genome region experimentally obtained, over which other indications have been superimposed, which indications illustrate the way in which the restriction enzyme and the sequence of bases belonging to the oligonucleotides used as primers have been chosen.

The fringe of two lines (in the FIG. 1) must be taken as continuous and read from left to right and from upwards to downwards, like reading usual writing.

In the upper line, a sequence of bases of one of the strands of a DNA fragment of the Y chromosome is shown, from extreme 5' end to the extreme 3' end, whereas in the lower line the same was done with the strand corresponding to that chromosome. The complementary chains have not been represented.

The bases have been symbolized as usual as follows:

A=adenine, T=thymine, G=guanine and C=cytosine. The symbols ? and X represent different types of indeterminations. The complementary strands not illustrated are corresponded base to base, such as base A from one, with base T from the other, and base G from one with base C from the other. Besides, they are antiparallel, that is, the extreme that corresponds to -5'- of the illustrated chains is the -3'- of the complementary, and visa versa.

It is possible to appreciate that the sequences of chromosome Y and chromosome X differ in some bases, whereas in the majority of bases in the homologous region they coincide.

The following step was to look for a restriction enzyme able to cut the Y chromosome fragment at a certain point but unable to do so on the X chromosome fragment. After many tests, the enzyme PstI was chosen, which is able to distinguish the sequence CTGCAG, referred to with the letter -∝-, and cut it between bases C and T. On the other hand, this sequence has got as its complement the sequence GACGTC, but this sequence, read in the direction 5'3' of the complement, is the same sequence CTGCAG, which is also cut by the enzyme PstI between the C and the T. But, in the corresponding position, the X chromosome has the sequence CCGCAG which is not recognized by the enzyme.

The advantage of choosing the enzyme PstI is that the sequence it recognizes doesn't repeat all over the amplified fragment, and as a consequence there is only one cut in the fragment obtained from Y chromosome and none in the fragment obtained from the X chromosome.

Sequences of extreme bases, referred to as -XY/1- and its complementary -XY/2- were chosen for the amplification (the last one -XY/2- is read from right to left, as it corresponds to the antiparallel chain, and therefore from its extreme 5' to 3'): for example, 5'-ATAATCACATGGAGAGCCACAAGCT-3' (SEQ. ID. NO: 3) and 5'-GCACTTCTTTGGTATCTGAGAAAGT-3', (SEQ. ID. NO: 4) are the first pair of oligonucleotide primers.

The extremes -T- of both are the 3' extremes from which the DNA fragments are copied.

To be able to further amplify the fragments that are a copy of the X or Y chromosome, as a result of the PCR amplification, and not copies of any unrelated DNA fragment, the same primers cannot be used again, because all of the fragments would be copied, instead of only the desired target fragments. Such unrelated DNA fragments may originate from contaminants.

The second round of PCR was carried out with primers that were taken from the extremes of an internal fragment belonging to the selected fragment in the first round of amplification and excluding sequences from the first oligonucleotide primers. In this way, the -N/XY 1- sequence and the complement to -N/XY 2- (and in inverse order), as shown in FIG. 1 as follows: 5'-TTGAATGTGATGAGT- GTGGG-3' and 5'-AAGTCAGAAGACAAATGT-CA-3', (SEQ. ID. NO: 5 and 6) were chosen, obtaining the second pair of oligonucleotide primers.

The oligonucleotide primers for the first, as well as for the second PCR reaction were synthesized in a "gene assembler" device.

Returning to the PCR technique, to the aqueous DNA solution 20 µl of buffer was added, containing in a final concentration of 10 mM of potassium chloride, 10mM of ammonium sulfate, 20 mM tris pH 8.8, 2 mM of magnesium sulfate, 0.1% of triton X-100, 100 µg/ml of bovine albumin, 0.2 mM of nucleotide dTTP, 0.2 mM of nucleotide dCTP, 0.2 mM of nucleotide dATP, 0.2 mM of nucleotide dGTP, 300 µg of each one of the first pair of oligonucleotides, and 1.5 units of the DNA polymerase enzyme of Thermus aquaticus;

covering with 50 µl of mineral oil;

repeating 45 times the following cycle:
    denaturing for 30 seconds at 93° C.;
    letting oligonucleotide primers anneal to the homologous regions of the DNA to be amplified for 30 seconds at 60° C.;
    amplifying for one minute at 72°.

The first solution of amplified DNA is thus obtained.

Then follows the second round of the polymerase chain reaction, which includes the next steps:

taking one aliquot of 30 µl of the amplified DNA's first solution;

adding 20 µl of buffer to the tube, containing, in final concentration, 10 mM of potassium chloride, 10 mM of ammonium sulfate, 20 mM Tris pH 8.8, 2 mM of magnesium sulfate, 0.1% of Triton X-100, 100 µg/ml of bovine albumin, 0.2 mM of dTTP, 0.2 mM of dCTP, 0.2 mM of dATP, 0.2 mM of dGTP, 300 µg of each one of the second pair of oligonucleotides, and 1.5 units of the DNA polymerase enzyme of *Thermus aquaticus;* covering with 50 µl of mineral oil;

repeating 45 times the following cycle denaturing during 30 seconds at 93° C.;

letting oligonucleotides anneal to the homologous regions of the DNA to be amplified during 30 seconds at 60° C.;

amplifying for one minute at 72° C.;

(In this way, the second solution of amplified DNA is obtained.)

adding 5 units of the restriction enzyme Pst1, digesting for two hours;

fractionating according to size subjecting the samples to electrophoresis on a 2% agarose gel, at 100 volts for 2 hours; staining with ethidium bromide and visualizing with UV (ultraviolet) light, and comparing bands obtained with a standard molecular weight marker.

If the embryo's sex would have been female, it would have 2 X chromosomes per cell and one only band would be obtained, corresponding to 378 bases pairs. This is shown in FIG. 1. The 378 base pairs correspond to the fragment that begins at the outer extreme of -N/XY 1-, up to the outer extreme of -N/XY 2- of the X chromosome. If, on the other hand, the embryo's sex would have been male, containing therefore one X chromosome and one Y chromosome per cell, there would have been a first band of 378 base pairs bases (corresponding to the X chromosome), a second band of 293 base pairs (between the extreme of -N/XY 1- and the cut -∞- made by Pst1) and a third band of 85 base pairs (between the cut -∞- and the extreme of -N / XY 2 -) (corresponding to the Y chromosome).

It is obvious that an enzyme which produces a cut in the DNA chair of the X chromosome and not in the DNA of the Y chromosome would also allow the determination of the sex according to the present invention, but with the following difference:

In the case of a female embryo, there would be obtained 2 bands with a number of base pairs which add up and which would correspond to the internal fragment; in the case of a male embryo, there would be obtained 3 bands.

In this way, an example of the performance of the procedure to determine the sex of mammal's embryos has been described as an embodiment of the present invention, as depicted by the following claims.

It is to be noted, that other modifications to the present invention may be obtained, without departing from the spirit and scope of the present invention, as noted in the appended claims.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 447 base pairs
        ( B ) TYPE: nucleic acid
        ( C ) STRANDEDNESS: double
        ( D ) TOPOLOGY: linear ( i i ) MOLECULE TYPE: genomic DNA ( i v ) ANTI-SENSE: no ( v i ) ORIGINAL SOURCE:
        ( A ) ORGANISM: bovine
        ( B ) STRAIN: European races
        ( C ) INDIVIDUAL ISOLATE: male bovine
        ( D ) DEVELOPMENTAL STAGE: adults
        ( E ) HAPLOTYPE: diploide (F) TISSUE TYPE: blood
(G) CELL TYPE: nucleated cell (vii) IMMEDIATE SOURCE:
(A) LIBRARY: genomic
(B) CLONE: ZFY clones obtained by PCR amplification techniques (viii) POSITION IN GENOME:
(A) CHROMOSOME/SEGMENT: chromosome Y/short arm
(B) MAP POSITION: not determined (ix) FEATURE:
(A) NAME/KEY: sequence of bases of one of the chains of a DNA fragment of chromosome Y
(B) LOCATION: not determined
(C) IDENTIFICATION METHOD: it was cloned and identified by using information corresponding to homologous sequences present in human genome
(D) OTHER INFORMATION: it contains polymorphisms that allow sex determination (x) PUBLICATION INFORMATION:
(A) AUTHORS: Pollevick, Guido D.
Giambiagi, Susana
Mancardi, Sabrina
De Luca, Leonardo
Burrone, Oscar
Frash, Alberto C.
Ugalde, Rodolfo A.
(B) TITLE: Sex determination of bobine embryos by restriction fragment polymorphisms of PCR amplified ZFX/ZFY loci
(C) JOURNAL: Bio/Technology
(D) VOLUME: 10
(E) ISSUE: No. 7
(F) PAGES: 805 to 807
(G) DATE: July 1992
(K) RELEVANT RESIDUES IN SEQ ID NO: from 1 to 447

(xi) SEQUENCE DESCRIPTION: SEQ ID NO: 1:

```
ATAATCACAT GGAGAGCCAC AAGCTTACCA GCAAGTCAGA GAAGGCCATC GAATGTGATG      60
ACTGTGGGAA GCATTTCTCC CATGCTGGGG CTTTGTTCAC TCACAAAATG GTGCATAAGG    120
AAAAAGGAGC CAGCAAAATG CATAAATGTA AATTCTGTGA GTATGAGACA GCTGAACAAG    180
GGTTATTAAA TCGCCACCTT TTGGCAGTCC ACAGCAAGAA CTTTCCCCAT ATATGTGTAG    240
AGTGTGGTAA AGGTTTTCGT CACCCATCAG AGCTCAAAAA GCACATGCGA ATCCATACTG    300
GAGAGAAACC GTACCAATGC CAGTACTGCG AATATAGGTC TGCAGACTCT TCTAATTTGA    360
AGACGCATGT GAAAACTAAG CATAGTAAAG AAATGTCTTT CAAGTGTGAC ATTTGTCTTC    420
TGACTTTCTC AGATACCAAA GAAGTGC                                       447
```

(2) INFORMATION FOR SEQ ID NO: 2:

(i) SEQUENCE CHARACTERISTICS:
(A) LENGTH: 447 base pairs
(B) TYPE: nucleic acid
(C) STRANDEDNESS: double
(D) TOPOLOGY: linear (ii) MOLECULE TYPE: genomic DNA (iv) ANTI-SENSE: no (vi) ORIGINAL SOURCE:
(A) ORGANISM: bovine
(B) STRAIN: European races
(C) INDIVIDUAL ISOLATE: male and female bovine
(D) DEVELOPMENTAL STAGE: adults
(E) HAPLOTYPE: diploide
(F) TISSUE TYPE: blood
(G) CELL TYPE: nucleated cell (vii) IMMEDIATE SOURCE:
(A) LIBRARY: genomic (B) CLONE: ZFX clones obtained by PCR amplification techniques (viii) POSITION IN GENOME:
    (A) CHROMOSOME/SEGMENT: chromosome X/short arm
    (B) MAP POSITION: not determined (ix) FEATURE:
    (A) NAME/KEY: sequence of bases of one of the chains of a DNA fragment of chromosome X
    (B) LOCATION: not determined
    (C) IDENTIFICATION METHOD: it was cloned and identified by using information corresponding to homologous sequences present in human genome
    (D) OTHER INFORMATION: it contains polymorphisms that allow sex determination (x) PUBLICATION INFORMATION:
    (A) AUTHORS: Pollevick, Guido D.
                   Giambiagi, Susana
                   Mancardi, Sabrina
                   De Luca, Leonardo
                   Burrone, Oscar
                   Frash, Alberto C.
                   Ugalde, Rodolfo A.
    (B) TITLE: Sex determination of bobine embryos by restriction fragment polymorphisms of PCR amplified ZFX/ZFY loci
    (C) JOURNAL: Bio/Technology
    (D) VOLUME: 10
    (E) ISSUE: No. 7
    (F) PAGES: 805 to 807
    (G) DATE: July 1992
    (K) RELEVANT RESIDUES IN SEQ ID NO: from 1 to 447

(xi) SEQUENCE DESCRIPTION: SEQ ID NO: 2:

```
ATAATCACAT GGAGAGCCAC AAGCTTACCA GCAAGGCGGA GAAGGCCATT GAATGCGATG      60

AGTGCGGGAA GCATTTCTCT CATGCTGGGG CTTTGTTTAC TCATAAAATG GTGCATAAGG    120

AAAAAGGAGC TAACAAAATG CACAAATGTA AATTCTGTGA ATACGAGACA GCTGAACAAG    180

GGTTACTGAA TCGCCACCTT TTGGCGGTCC ATAGCAAGAA CTTTCTCCAT ATACGTGTGG    240

AGTGTGGTAA AGGTTTTCGT CATCCATCAG AGCTCAAAAA GCACATGCGA ATCCATACTG    300

GCGAGAAGCC GTACCAGTGC CAGTACTGCG AATATAGGTC CGCAGACTCT TCTAACTTGA    360

AAACGCATGT AAAAACTAAG CATAGTAAAG AGATGCCATT CAAGTGTGAC ATTTGTCTTC    420

TGACTTTCTC AGATACCAAA GAAGTGC                                        447
```

(2) INFORMATION FOR SEQ ID NO: 3:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: synthetic nucleic acid
        (A) DESCRIPTION:
            The sequence was choiced following the rules of the present invention (applied for bovines) and was synthesized in a 'gene assembler'device, to be one of the primers for the first amplification stage.

(iv) ANTI-SENSE: no (vi) ORIGINAL SOURCE:
        (A) ORGANISM: bovine
        (B) STRAIN: European races
        (C) INDIVIDUAL ISOLATE: male bovine
        (D) DEVELOPMENTAL STAGE: adults
        (E) HAPLOTYPE: diploide
        (F) TISSUE TYPE: blood
        (G) CELL TYPE: nucleated cell (vii) IMMEDIATE SOURCE:
        (A) LIBRARY: genomic (B) CLONE: ZFY clones obtained by PCR amplification techniques (viii) POSITION IN GENOME:
    (A) CHROMOSOME/SEGMENT: chromosome X or Y/short arm
    (B) MAP POSITION: not determined
    (C) UNITS: bases (ix) FEATURE:
    (A) NAME/KEY: one of oligonucleotides of the first pair,
        complementary with the extreme 3'of one of the
        complementary chains of the first fragment of the sexual
        chromosome of bovines (sequences No. 1 and 2)
    (D) OTHER INFORMATION: it allow amplification of the first
        fragment of the sexual chromosome of bovines.

(x) PUBLICATION INFORMATION:
    (A) AUTHORS: Pollevick, Guido D.
        Giambiagi, Susana
        Mancardi, Sabrina
        De Luca, Leonardo
        Burrone, Oscar
        Frash, Alberto C.
        Ugalde, Rodolfo A.
    (B) TITLE: Sex determination of bobine embryos by restriction
        fragment polymorphisms of PCR amplified ZFX/ZFY loci
    (C) JOURNAL: Bio/Technology
    (D) VOLUME: 10
    (E) ISSUE: No. 7
    (F) PAGES: 805 to 807
    (G) DATE: July 1992
    (K) RELEVANT RESIDUES IN SEQ ID NO: from 1 to 25

(xi) SEQUENCE DESCRIPTION: SEQ ID NO: 3:

ATAATCACAT GGAGAGCCAC AAGCT        25

(2) INFORMATION FOR SEQ ID NO: 4:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: synthetic nucleic acid
        (A) DESCRIPTION:
            The sequence was choiced following the rules of the
            present invention (applied for bovines) and was
            synthesized in a 'gene assembler'device, to be one of
            the primers for the first amplification stage.

(iv) ANTI-SENSE: no (vi) ORIGINAL SOURCE:
        (A) ORGANISM: bovine
        (B) STRAIN: European races
        (C) INDIVIDUAL ISOLATE: male bovine
        (D) DEVELOPMENTAL STAGE: adults
        (E) HAPLOTYPE: diploide
        (F) TISSUE TYPE: blood
        (G) CELL TYPE: nucleated cell (vii) IMMEDIATE SOURCE:
        (A) LIBRARY: genomic
        (B) CLONE: ZFY clones obtained by PCR amplification techniques (viii) POSITION IN GENOME:
        (A) CHROMOSOME/SEGMENT: chromosome X or Y/short arm
        (B) MAP POSITION: not determined
        (C) UNITS: bases (ix) FEATURE:
        (A) NAME/KEY: one of oligonucleotides of the first pair,
            complementary with the extreme 3'of one of the
            complementary chains of the first fragment of the sexual
            chromosome of bovines (sequences No. 1 and 2)
        (D) OTHER INFORMATION: it allow amplification of the first
            fragment of the sexual chromosome of bovines.

(x) PUBLICATION INFORMATION:
(A) AUTHORS: Pollevick, Guido D.
Giambiagi, Susana
Mancardi, Sabrina
De Luca, Leonardo
Burrone, Oscar
Frash, Alberto C.
Ugalde, Rodolfo A.
(B) TITLE: Sex determination of bobine embryos by restriction
fragment polymorphisms of PCR amplified ZFX/ZFY loci
(C) JOURNAL: Bio/Technology
(D) VOLUME: 10
(E) ISSUE: No. 7
(F) PAGES: 805 to 807
(G) DATE: July 1992
(K) RELEVANT RESIDUES IN SEQ ID NO: from 1 to 25

(xi) SEQUENCE DESCRIPTION: SEQ ID NO: 4:

GCACTTCTTT GGTATCTGAG AAAGT         25

(2) INFORMATION FOR SEQ ID NO: 5:

(i) SEQUENCE CHARACTERISTICS:
(A) LENGTH: 20 bases
(B) TYPE: nucleic acid
(C) STRANDEDNESS: single
(D) TOPOLOGY: linear (ii) MOLECULE TYPE: synthetic nucleic acid
(A) DESCRIPTION:
The sequence was choiced following the rules of the
present invention (applied for bovines) and was
synthesized in a 'gene assembler'device, to be one of
the primers for the second amplification stage.

(iv) ANTI-SENSE: no (vi) ORIGINAL SOURCE:
(A) ORGANISM: bovine
(B) STRAIN: European races
(C) INDIVIDUAL ISOLATE: male bovine
(D) DEVELOPMENTAL STAGE: adults
(E) HAPLOTYPE: diploide
(F) TISSUE TYPE: blood
(G) CELL TYPE: nucleated cell (vii) IMMEDIATE SOURCE:
(A) LIBRARY: genomic
(B) CLONE: ZFY clones obtained by PCR amplification techniques (viii) POSITION IN GENOME:
(A) CHROMOSOME/SEGMENT: chromosome X or Y/short arm
(B) MAP POSITION: not determined
(C) UNITS: bases (ix) FEATURE:
(A) NAME/KEY: one of oligonucleotides of the second pair,
complementary with the extreme 3'of one of the
complementary chains of the second fragment (internal
to the first fragment) of the sexual chromosome of
bovines.
(D) OTHER INFORMATION: it allow amplification of the second
fragment of the sexual chromosome of bovines.

(x) PUBLICATION INFORMATION:
(A) AUTHORS: Pollevick, Guido D.
Giambiagi, Susana
Mancardi, Sabrina
De Luca, Leonardo
Burrone, Oscar
Frash, Alberto C.
Ugalde, Rodolfo A.
(B) TITLE: Sex determination of bobine embryos by restriction
fragment polymorphisms of PCR amplified ZFX/ZFY loci
(C) JOURNAL: Bio/Technology
(D) VOLUME: 10
(E) ISSUE: No. 7
(F) PAGES: 805 to 807

(G) DATE: July 1992
(K) RELEVANT RESIDUES IN SEQ ID NO: from 1 to 20

(xi) SEQUENCE DESCRIPTION: SEQ ID NO: 5:

TTGAATGTGA TGAGTGTGGG                        20

(2) INFORMATION FOR SEQ ID NO: 6:

(i) SEQUENCE CHARACTERISTICS:
    (A) LENGTH: 20 bases
    (B) TYPE: nucleic acid
    (C) STRANDEDNESS: single
    (D) TOPOLOGY: linear (ii) MOLECULE TYPE: synthetic nucleic acid
    (A) DESCRIPTION:
        The sequence was choiced following the rules of the
        present invention (applied for bovines) and was
        synthesized in a 'gene assembler'device, to be one of
        the primers for the second amplification stage.

(iv) ANTI-SENSE: no (vi) ORIGINAL SOURCE:
    (A) ORGANISM: bovine
    (B) STRAIN: European races
    (C) INDIVIDUAL ISOLATE: male bovine
    (D) DEVELOPMENTAL STAGE: adults
    (E) HAPLOTYPE: diploide
    (F) TISSUE TYPE: blood
    (G) CELL TYPE: nucleated cell (vii) IMMEDIATE SOURCE:
    (A) LIBRARY: genomic
    (B) CLONE: ZFY clones obtained by PCR amplification techniques (viii) POSITION IN GENOME:
    (A) CHROMOSOME/SEGMENT: chromosome X or Y/short arm
    (B) MAP POSITION: not determined
    (C) UNITS: bases (ix) FEATURE:
    (A) NAME/KEY: one of oligonucleotides of the second pair,
        complementary with the extreme 3'of one of the
        complementary chains of the second fragment (internal
        to the first fragment) of the sexual chromosome of
        bovines.
    (D) OTHER INFORMATION: it allow amplification of the second
        fragment of the sexual chromosome of bovines.

(x) PUBLICATION INFORMATION:
    (A) AUTHORS: Pollevick, Guido D.
                 Giambiagi, Susana
                 Mancardi, Sabrina
                 De Luca, Leonardo
                 Burrone, Oscar
                 Frash, Alberto C.
                 Ugalde, Rodolfo A.
    (B) TITLE: Sex determination of bobine embryos by restriction
        fragment polymorphisms of PCR amplified ZFX/ZFY loci
    (C) JOURNAL: Bio/Technology
    (D) VOLUME: 10
    (E) ISSUE: No. 7
    (F) PAGES: 805 to 807
    (G) DATE: July 1992
    (K) RELEVANT RESIDUES IN SEQ ID NO: from 1 to 20

(xi) SEQUENCE DESCRIPTION: SEQ ID NO: 6:

AAGTCAGAAG ACAAATGTCA                        20

We claim:

1. A process for sex determination of embryos in bovines which comprises:

a) isolating a bovine embryo at the blastula stage;

b) cutting a zone of cells away from the pellucidae membrane of said embryo by microsurgery and extracting a sample of about 8 to about 19 cells from said zone of cells;

c) separating said about 8 to about 19 cells from remaining traces of the embryo's pellucidae membrane;

d) isolating DNA from said about 8 to about 19 cells by placing the sample in a tube with water, heating the contents of the tube to 95° C. to form an aqueous denatured DNA solution, immediately chilling the contents of said tube by placing the tube in ice, and centrifuging the contents of said tube to recover any condensed liquid containing the aqueous denatured DNA solution;

e) performing a first round of a polymerage chain reaction (PCR) on said aqueous denatured DNA solution to amplify a first fragment of DNA wherein said first fragment of DNA is a subsequence of a sequence in a homologous genome region of the X and Y chromosome, using a first pair of oligonucleotide primers with the sequence 5'-ATAATCACATGGAGAGCCA-CAAGCT-3' (SEQ. ID. NO:3) and 5'-CGACT-TCTTTGGTATCTGAGAAAGT-3' (SEQ. ID. NO:4), in the presence of a DNA polymerage enzyme and nucleotides until a solution of a first amplified DNA fragment is obtained;

f) obtaining an aliquot of said solution and subjecting said aliquot to a second round of PCR to amplify a second DNA fragment whose sequence is a subsequence of said first amplified DNA fragment using a second pair of oligonucleotide primers with the sequence: 5'-TTGAATGTGATGAGTGTGGG-3' (SEQ. ID. NO: 5) and 5'-AAGTCAGAAGACAAATGTCA-3' (SEQ. ID. NO: 6) until a solution of a second amplified DNA fragment is obtained;

g) digesting said second amplified DNA fragment with PstI, wherein the presence of a PstI cut site in said second amplified DNA fragment indicates the presence of a Y chromosome and wherein the absence of a PstI cut site in said second amplified DNA fragment indicates the presence of an X chromosome, thereby forming a mixture of cut and/or uncut second amplified DNA fragments;

h) size separating said mixture of cut and/or uncut second amplified DNA fragments by electrophoresis on a 2% agarose gel and determining the size of digested fragments by a comparison of bands obtained on said gel with a standard molecular weight marker wherein the presence of a 378 base pair band is indicative of the presence of an X chromosome and the presence of two bands which are 293 base pairs and 85 base pairs each is indicative of the presence of a Y chromosome;

i) determining the sex of the embryo based on results obtained in step (h).

2. The process as in claim 1, wherein at step (g), 5 units of PstI is used and digestion is performed for 2 hours.

* * * * *